United States Patent [19]
Hopkins

[11] Patent Number: 5,689,545
[45] Date of Patent: Nov. 18, 1997

[54] LASER LINE PROJECTING TOOL FOR LEVELING AND ALIGNMENT OF X-RAY EQUIPMENT, AND METHOD OF USE

[75] Inventor: Edwin Hopkins, Delafield, Wis.

[73] Assignee: U.S. Philips Corporation, New York, N.Y.

[21] Appl. No.: 573,167

[22] Filed: Dec. 15, 1995

[51] Int. Cl.$^6$ .................................................. A61B 6/08
[52] U.S. Cl. ........................... 378/206; 378/204; 378/205
[58] Field of Search ............................ 378/206, 205, 378/207, 204; 33/DIG. 21, 263, 279, 283, 286, 290, 366, 370, 371, 390

[56] References Cited

U.S. PATENT DOCUMENTS

| | | | |
|---|---|---|---|
| 4,255,657 | 3/1981 | Lescrenier | 378/206 |
| 4,836,671 | 6/1989 | Bautista | 378/206 X |
| 5,136,784 | 8/1992 | Marantz | 33/366 |
| 5,153,999 | 10/1992 | Sharpe et al. | 33/366 |
| 5,367,779 | 11/1994 | Lee | 33/290 |
| 5,539,990 | 7/1996 | Le | 33/DIG. 21 |

*Primary Examiner*—David P. Porta
*Attorney, Agent, or Firm*—Jack D. Slobod

[57] ABSTRACT

A portable battery powered tool for aligning equipment in an X-ray room includes two spaced apart channel engaging connectors carried by a reference surface of the tool for engaging the usual recessed channels in the ceiling of the X-ray room, a laser carried by the tool for projecting a line in a projection plane parallel to the reference surface and an electronic sensor and indicator carried by the tool for indicating with an array of LEDs whether the projection plane deviates from level along each of two orthogonal axes. The tool also includes adjustment screws for finely adjusting the orientation of the reference surface relative to the ceiling. When mounted to the ceiling and leveled, the tool projects a line on a surface of the rail which projected line is used as a reference for leveling the rail. A stand is provided for the tool to establish a vertical projection plane so as to produce corresponding projected lines on the floor and ceiling. The tool also has a flange for being mounted to the collimator of an overhead X-ray source so that it may facilitate longitudinal alignment of the source relative to the top of a patient table below.

8 Claims, 5 Drawing Sheets

LASER LINE PROJECTING TOOL FOR LEVELING AND ALIGNMENT OF X-RAY EQUIPMENT, AND METHOD OF USE

BACKGROUND OF THE INVENTION

1. Field of the Invention

The present invention relates generally to tools and methods for accurately aligning and leveling X-ray equipment and associated parts during an installation in an X-ray room.

2. Description of the Related Art

Generally an X-ray room as in a hospital or other medical imaging facility is constructed with a ceiling having parallel recessed channels of a type sold by Unistrut Corporation of Wayne Mich. under the trademark "Unistrut" for the mounting of overhead equipment. Also, a table floor plate may be included in the X-ray room as constructed for the mounting of an X-ray patient table thereon. Thereafter, the X-ray equipment and associated overhead rails and bridges between rails are installed, generally by the medical equipment provider, utilizing the pre-existing ceiling channels and floor plate. The task of accurately positioning and aligning the X-ray equipment and associated overhead rails and bridges during such installations is quite time consuming. Prior methods required the use of plumb-bobs, transits or water levels, and a significant amount of measuring.

SUMMARY OF THE INVENTION

It is a general object of the present invention to significantly reduce the time needed utilizing prior alignment and locating methods for installing X-ray equipment and associated overhead parts by providing a specialized portable tool for projecting one or more visible bright lines of desired orientation on pertinent vertical and/or horizontal surfaces;

It is a further object of the present invention that the tool be useful for leveling rails and for aligning of an overhead suspension to a patient table;

It is yet another object of the present invention that said tool include an integral easily readable means for aligning the projected line to be level and further that it be configured for mounting or placement with respect to the pertinent surfaces or equipment encountered in an X-ray room including the "unistrut" ceiling channel.

Briefly, these and other objects are satisfied by providing a portable battery powered tool including a laser line projector which is precision aligned with a dual-axis electronic level sensor and indicator. The line projector actually projects light in a projection plane which is parallel to a reference surface of the tool. The level indicator is in the form of an array of lights showing the direction of deviation of the reference surface from level (which corresponds to the deviation of the projection plane from level) along two orthogonal axes. The tool includes two spaced apart "unistrut" engaging connectors carried by the reference surface for engaging the usual parallel recessed "unistrut" channels in the ceiling of the X-ray room and fine adjustment screws for precisely orienting the reference surface (and thereby, the projection plane) relative to the ceiling.

For leveling ceiling mounted rails the tool is mounted extending between and generally perpendicular to two ceiling "unistrut" channels and adjusted to level by manipulating the fine adjustment screws while observing the indicator lights until a level condition is indicated along both axes of the level sensor. The laser line generator is turned on to project a horizontal line on the vertical side surface of a rail also mounted to the ceiling channels. This rail is shimmed while observing the projecting line on its side.

For precisely installing an overhead installation and a patient table which are to be aligned with each other, the tool of the present invention may be utilized to simultaneously project lines on the floor and ceiling which lie in the same vertical plane. In this connection, the tool is mounted to a stand. The line on the floor may be directed along a pertinent part of a table floor plate and the corresponding line on the ceiling may be used for locating a rail or a bridge between rails.

The tool of the present invention is also useful for aligning an overhead installation such as an X-ray source relative to a patient table below. For this purpose, the tool is also configured for mounting to the collimator of the X-ray source such that it downwardly projects a line on the table top or edge below intended to be parallel to the longitudinal direction of the table.

BRIEF DESCRIPTION OF THE DRAWING

Other objects, features and advantages of the present invention will become apparent upon perusal of the following detailed description when taken in conjunction with the appended drawing, wherein.

DETAILED DESCRIPTION OF THE PREFERRED EMBODIMENTS

Figure 1:
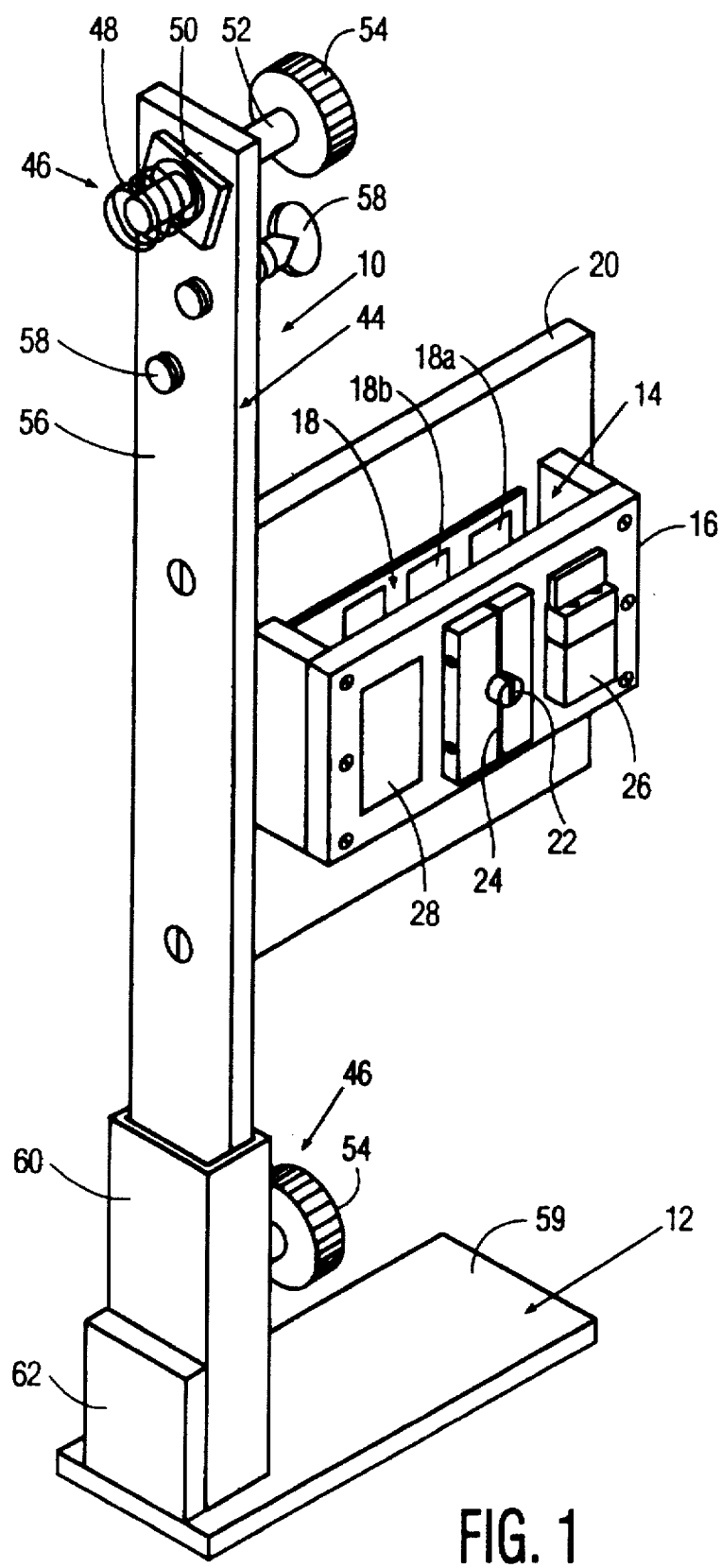
FIG. 1 is an isometric view of the tool of the present invention oriented for producing a vertical projection plane and utilizing a stand for support.
Figure 2:
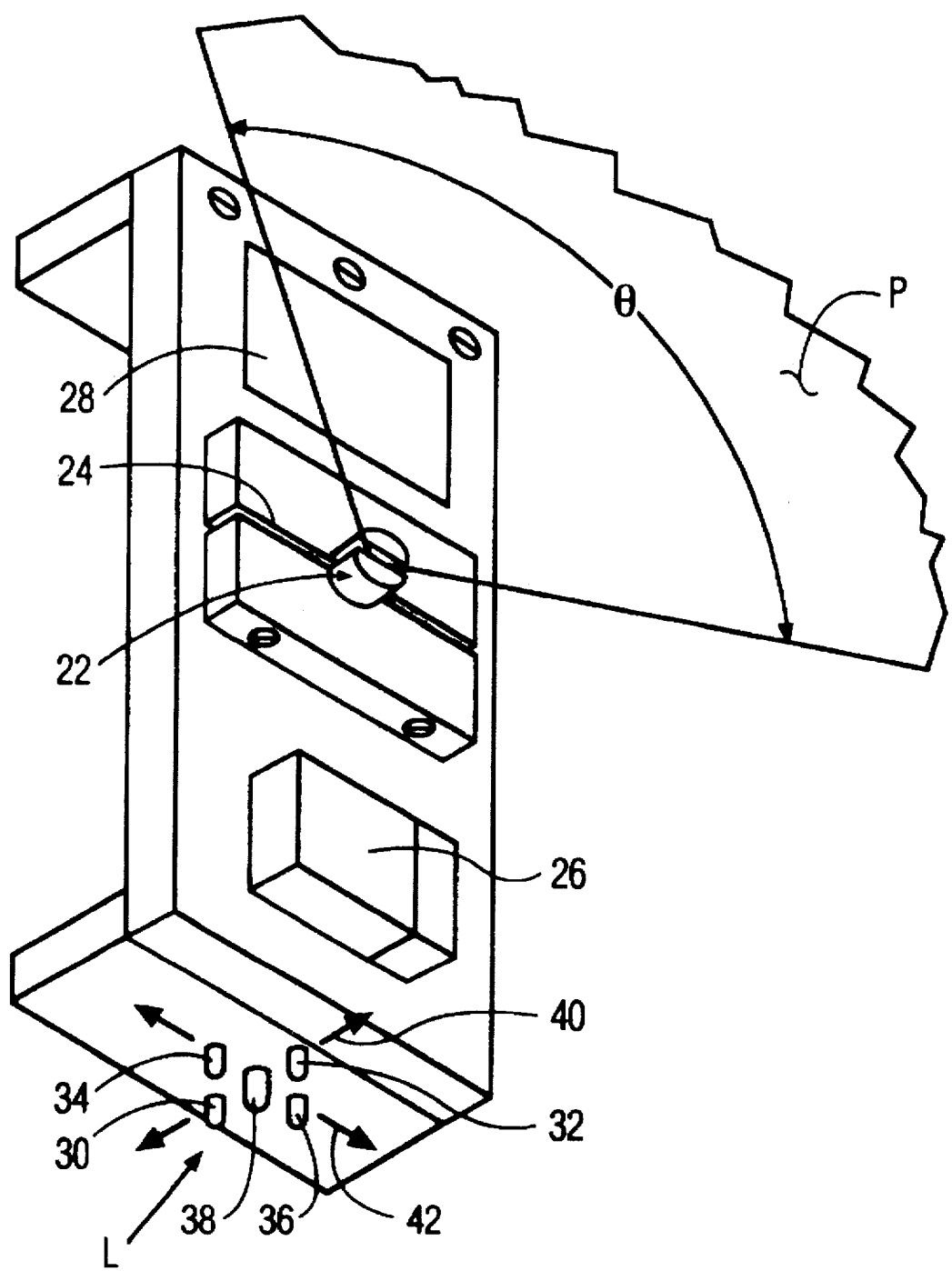
FIG. 2 is an isometric view of an electronics cover portion of the tool of FIG. 1 oriented for producing a horizontal projection plane.

Referring first to FIGS. 1 and 2, there is shown the alignment tool 10 of the present invention in conjunction with a separate stand 12 in which tool 10 may be fixedly supported. Tool 10 includes an electronics section 14 in the form of a cover portion 16 and circuit boards 18, each mounted to a flanged plate 20. Cover portion 16 carries at its front a line projector 22 in the form of a visible laser diode module and cylindrical lens. The diode module projects laser light in a fan shaped projection plane P perpendicular to the front of cover portion 16 which projection plane is aligned with a slit 24 in module 22. The projected light preferably has an included angle in the projection plane P of about 80° so that it fans out at reasonable distances to project lines approaching room dimensions in length. A suitable-laser diode module is available from Applied Laser Systems Grants Pass, Oregon as model no. VLM2.3-3L. Such laser module utilizes an InGaAlp semiconductor laser, and nominally produces 2.5 mW at 6.35 nm wavelength.

Cover portion 16 also carries at its front a compartment 26 for receiving a conventional 9 volt rectangular battery and a laser warning label 28 alerting the user to avoid direct eye exposure. On a side of the cover portion which is parallel to the projection plane P, there is an LED cluster L of four preferably red LED indicator lights 30, 32, 34 and 36 and a central preferably green LED indicator light 38. Lights 30 and 32 are aligned along a first axis 40 and lights 34, 36 are aligned along a second axis 42 orthogonal to the first axis. When the tool 10 is oriented with the cover portion 16 as shown in FIG. 2, the purpose of the downwardly facing indicator LEDs 30, 32, 34, 36 and 38 is to indicate by lighting one of LEDs 30, 32, the direction along axis 40 and by lighting one of LEDs 34, 36, the direction along axis 42, to slightly rotate tool 10 in order for the horizontal projection plane P to be level. When a level condition is attained, the central LED 38 lights. Circuit boards 18 include a dual axis tilt sensor board 18a and a comparator board 18b for controlling the LEDs 30, 32, 34, 36, and 38. Tilt sensor board 18a is available from the Fredericks Company of Huntington Valley, Pa. and utilizes a conventional liquid bias tube as the sensor, the board being oriented so that its two output voltages provide independent measures of angular deviation along axes 40 and 42. Preferably the sensitivity is adjusted such to provide full scale output voltages at deviations of ±2°. Comparator board 18b determines whether each output voltage of tilt sensor board 18b is positive or negative and lights the appropriate LEDs of 30, 32 and 34, 36 to indicate the direction(s) of movement needed for alignment or direction of misalignment. The output voltages are compared with zero (or a suitably small window about zero) so that when both voltages correspond to a null, the central LED 38 is lit indicating a level condition. This overall accuracy of the tilt sensor and comparator boards in indicating a level condition is preferably within ±2 arc minutes.

Tool 10 also has an elongated bar 44 screwed to flanged plate 20 which carries proximate its opposite ends connectors 46 configured for connection to "unistrut" channel as available from Unistrut Corporation, typically of the 1⅝ in. width size. As typically used for connection to such channel, each connector 46 includes a spring 48 and rectangular shaped nut 50 on a threaded rod 52 which is rotatable via the knob 54. The nut 50 may be inserted through a central slot in the channel so that after rotation by 90° it is captured in the channel and urged by spring 48 against reentrant portions thereof. The threaded rod 52 may then be rotated to tighten the connection so that reference surface 46 is held close but not necessarily tightly against the ceiling. The slight play available, allows for fine adjustment for leveling purposes along the axes 40, 42, utilizing two nylon screws 58 which are threaded through member 44 in order to adjustably bear against the ceiling.

The stand 12 includes a base 59 for resting on top of a horizontal surface. The lower end of member 44 is received in a channel 60 which includes at its bottom a short section 62 of "unistrut" channel into which the lower channel engaging connector is engaged in the usual manner.

Figure 3:
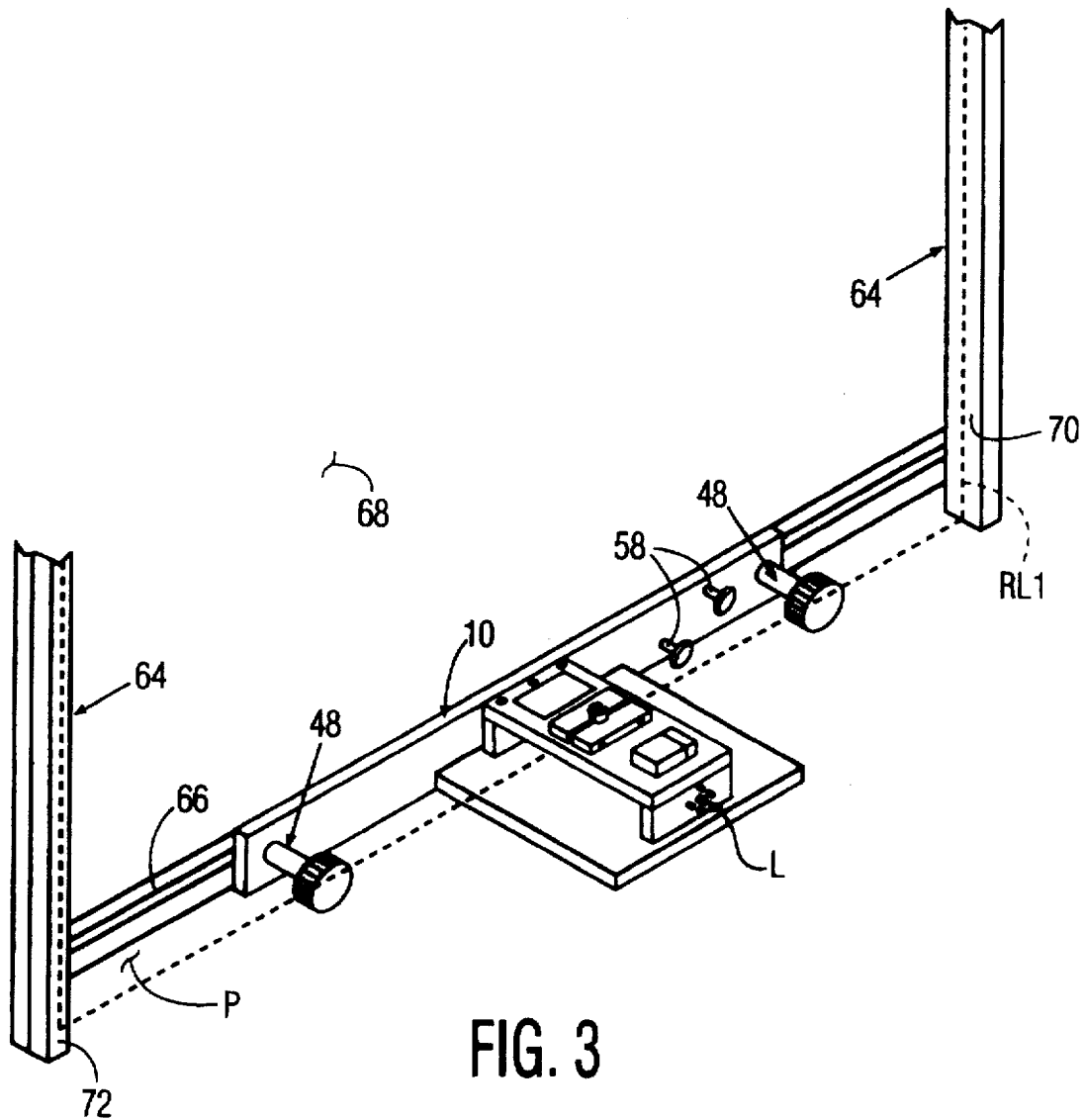
FIG. 3 is an isometric view of the tool of FIG. 1, without the stand, mounted for use in leveling rails.

As shown in FIG. 3, in order to use tool 10, less stand 12, for leveling rails 64 mounted to "unistrut" channel 66 in the ceiling 68 on X-ray room, the tool 10 is mounted to the "unistrut" channel via the channel engaging connectors 48 and leveled by manipulating fine adjustment screws 58 while observing LED cluster L until a level condition is indicated. The line projector 22 is then turned via a suitable switch (not shown) and projects a reference line RL1 along the vertically oriented side surface 70 of rail 64. The rail is then shimmed relative to ceiling 68 as necessary to make the longitudinal axis of the rail 64 parallel to the projected reference line. Alternatively, the projection plane may just graze the downwardly facing surface 72 of the rail 64 to produce the reference line RL2 thereon and prior to shimming rail 64 in the same manner.

Figure 4:
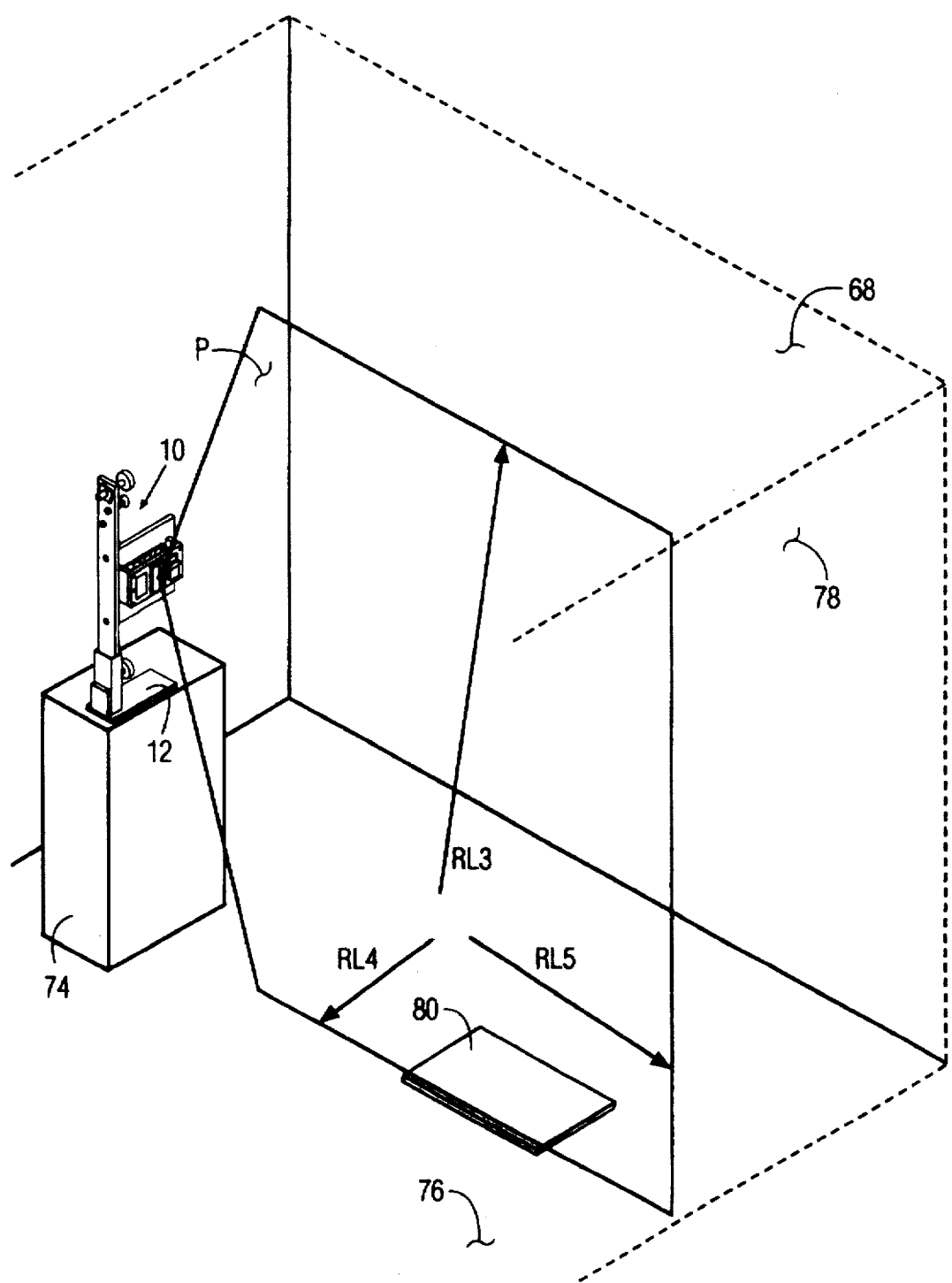
FIG. 4 is an isometric view of the tool of FIG. 1, including the stand, mounted for use in producing corresponding projected lines on floor and ceiling.

As shown in FIG. 4, the tool 10 is engaged in stand 12 and is placed on a floor stand 72 in order to produce a vertically oriented projection plane P projecting corresponding reference lines RL3, RL4 on the ceiling 68 and floor 70, respectively as well as a reference line RL5 on the vertical wall 78. The projection plane P may be positioned such that the projected reference line RL4 is along a predetermined line, such as an edge of table floor plate. The reference line RL3 may be advantageously used for locating rails and bridges between rails over a location where a patient table is installed.

Figure 5:
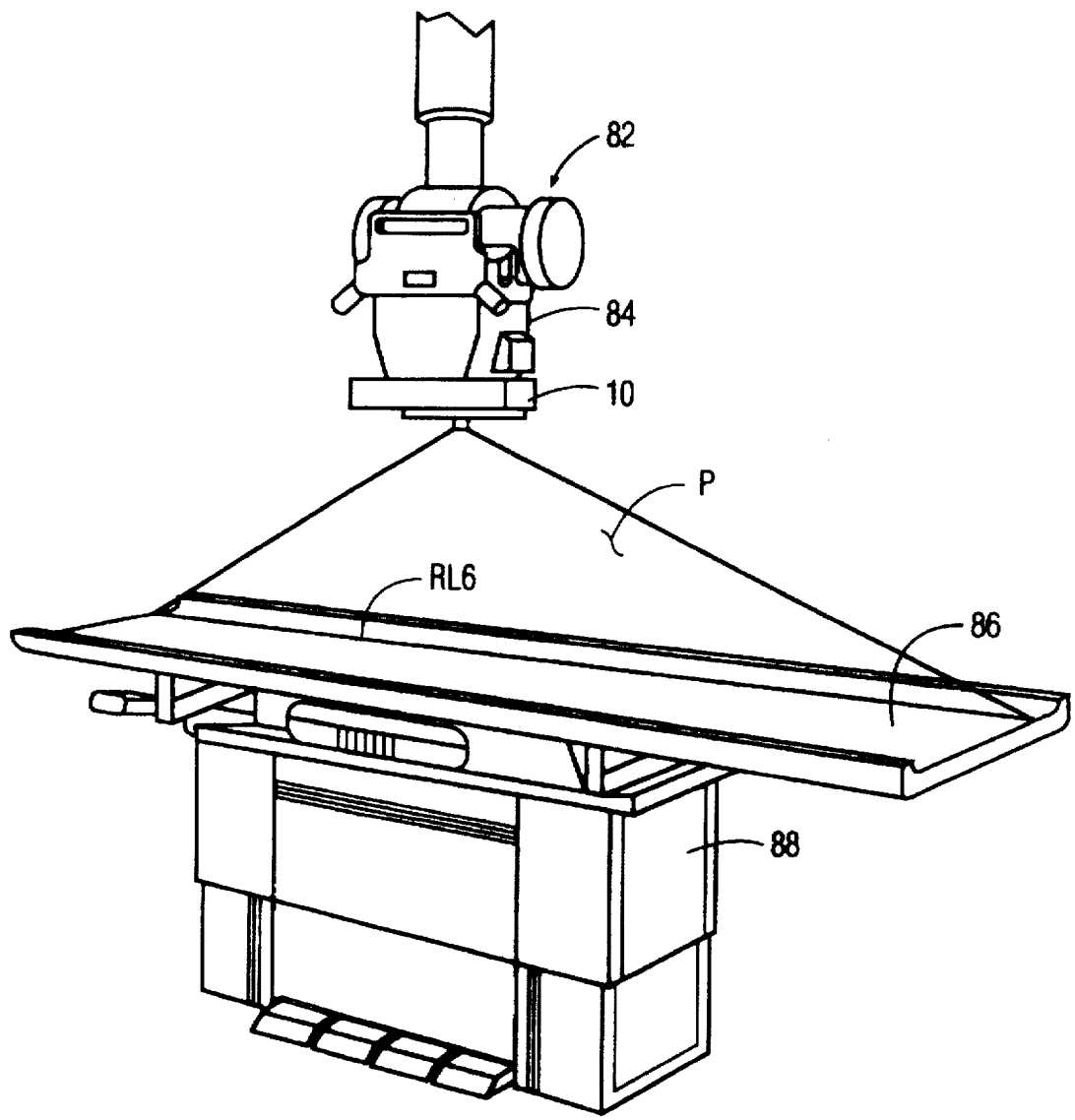
FIG. 5 is an isometric view of the tool of FIG. 1, without the stand, mounted for use in relatively aligning overhead equipment and a patient table.

After a superstructure has been installed suspended from leveled and oriented rails and bridges between rails, it is desirable to check and finally adjust, if necessary the orientation of the patient table before locking it to the table floor plate 80. The setup for this is illustrated in FIG. 5, where the superstructure or elevated equipment is in the form of an X-ray source including the usual collimator at the bottom. As is well known, X-ray source 82 is typically suspended from a trolley (not shown) attached to bridges (not shown) connected between ceiling mounted rails 64 so the X-ray source may be translated horizontally as desired or under motorized control. The flanged plate 20 of tool 10 is sized to be received snugly in the usual flange receiving slot in the collimator. When flange 20 is so received, tool 10 is oriented such that line projector 22 produces a downwardly directed vertical projection plane P which projects reference line RL6 on the table top 86 of patient table 88. Such a projected reference line is useful for checking or adjusting the longitudinal alignment of the patient table 88 relative to the X-ray source if there is a suitable elongated indicia or line on the table top 86 with which the reference line may be compared. Otherwise, the reference plane P may be located, through positioning of the X-ray source 82, to graze the edge of table top, whereby the edge may be examined to see if it is grazed by the projection plane throughout its length. It is also preferable that the longitudinal alignment between X-ray source and patient table be checked in this manner while also moving the X-ray source longitudinally.

Using the tool 10 according to the methods described herein have achieved significant savings of time, estimated to be in excess of five man hours per X-ray system installation. It should be apparent that the objects of the present invention have been achieved. It should also be understood that while the invention has been described in specific detail, numerous modification, additions or omissions in such details are possible within the intended spirit and scope of the invention.

What is claimed is:

1. A portable battery powered tool for aligning equipment in an X-ray room, comprising:
    mounting means carried by the tool for connecting the tool to an object;
    a light source carried by the tool for projecting a line in a projection plane; and
    electronic sensor and indicator means carried by the tool for indicating whether said projection plane deviates from horizontal in along each of two orthogonal axes;
    wherein said mounting means comprises a plurality of channel engaging connectors carried by a surface of the tool for engaging channel in the ceiling of the X-ray room.

2. The tool as claimed in claim 1, wherein said mounting means comprises a flange for engagement by an overhead X-ray source.

3. The tool as claimed in claim 2, further comprising a stand having a channel section for receiving said channel engaging connector to support said tool with said projection plane oriented vertically.

4. The tool as claimed in claim 1, further comprising adjustment means carried by the tool for, when the channel engaging connectors are engaging channel in the ceiling of the X-ray room, finely adjusting the orientation of the projection plane relative to the ceiling of the X-ray room.

5. The tool as claimed in claim 1, further comprising a stand comprising means for engaging said mounting means to support said tool with said projection plane oriented vertically.

6. A method of leveling a rail on a ceiling of an X-ray room, comprising:

mounting a line projecting light source to the ceiling such that a projection plane is horizontal and projects a line along a vertical side of the rail, and adjusting the orientation of the rail relative to the ceiling so that its longitudinal axis is parallel to the projected line.

7. A method of relatively aligning overhead equipment and a patient table having an elongated top below the equipment comprising:

mounting a line projecting light source to the overhead equipment so that it downwardly projects a line on the top of the patient table, and adjusting the relative orientation between the overhead equipment and the patient table such that a longitudinal axis of the patient table is parallel to the projected line on the table.

8. The method as claimed in claim 7, wherein said overhead equipment is an X-ray source including a collimator and said mounting is to said collimator.

* * * * *